US007345163B2

(12) United States Patent
Kwiatkowski

(10) Patent No.: US 7,345,163 B2
(45) Date of Patent: Mar. 18, 2008

(54) PROCESS FOR SEPARATING AND DEPROTECTING OLIGONUCLEOTIDES

(75) Inventor: Marek Kwiatkowski, Uppsala (SE)

(73) Assignee: Quiatech AB, Uppsala (SE)

( * ) Notice: Subject to any disclaimer, the term of this patent is extended or adjusted under 35 U.S.C. 154(b) by 319 days.

(21) Appl. No.: 10/229,485

(22) Filed: Aug. 28, 2002

(65) Prior Publication Data

US 2004/0044195 A1    Mar. 4, 2004

(51) Int. Cl.
*C07H 21/00* (2006.01)
(52) U.S. Cl. ............... 536/25.31; 536/25.4; 536/25.41; 536/25.42
(58) Field of Classification Search ............... 536/25.4, 536/25.41, 25.42, 25.3–25.31; 435/6
See application file for complete search history.

(56) References Cited

U.S. PATENT DOCUMENTS

| | | | |
|---|---|---|---|
| 4,997,927 A | | 3/1991 | Blocker et al. |
| 5,319,079 A | | 6/1994 | Reddy et al. |
| 5,547,941 A | * | 8/1996 | Battistini et al. ............. 514/44 |
| 5,567,604 A | * | 10/1996 | Rando et al. ............... 435/238 |
| 5,892,007 A | | 4/1999 | Ramage |
| 6,001,966 A | * | 12/1999 | Pieken et al. ............... 530/338 |
| 6,034,233 A | * | 3/2000 | Ecker et al. ............... 536/24.5 |
| 6,232,463 B1 | * | 5/2001 | Cook et al. ............... 536/25.3 |
| 6,255,475 B1 | | 7/2001 | Kwiatkowski |
| 6,262,251 B1 | * | 7/2001 | Pieken et al. ............... 536/25.3 |
| 6,291,669 B1 | | 9/2001 | Kwiatkowski et al. |
| 6,309,836 B1 | | 10/2001 | Kwiatkowski |
| 6,313,284 B1 | | 11/2001 | Kwiatkowski et al. |
| 6,608,035 B1 | * | 8/2003 | Agrawal et al. ............. 514/44 |
| 6,664,388 B2 | * | 12/2003 | Nelson .................... 536/25.31 |
| 2003/0153741 A1 | * | 8/2003 | Kwiatkowski ............. 536/25.4 |

FOREIGN PATENT DOCUMENTS

| | | |
|---|---|---|
| WO | WO 92/09615 | 6/1992 |
| WO | WO 98/03646 A1 * | 1/1998 |
| WO | WO 98/08857 | 3/1998 |
| WO | WO 98/51698 | 11/1998 |
| WO | WO 99/00401 A1 * | 1/1999 |
| WO | WO 99/09154 A2 * | 2/1999 |
| WO | WO 03/066651 A1 | 8/2003 |

OTHER PUBLICATIONS

Gait et al., "Synthesis of Oligodeoxyribonucleotides by a Continuous Flow, Phosphotriester Method on a Kiesselguhr/Polyamide Suppport," part of *Chemical & Enzymatic Synthesis of Gene Fragments: A Laboratory Manual*, Gassen & Lang (eds.), Verlag Chemie, Weinheim, DE, 1982, pp. 1-42.*

Seliger et al., "Solid-Phase Synthesis of Oligonucleotides Using the Phosphite Method," part of *Chemical & Enzymatic Synthesis of Gene Fragments: A Laboratory Manual*, Gassen & Lang (eds.), Verlag Chemie, Weinheim, W. Germany, 1982, pp. 81-96.*

Winnacker et al., "Solid-Phase Synthesis of Oligonucleoitdes Using the Phosphoramidite Method," part of *Chemical & Enzymatic Synthesis of Gene Fragments: A Laboratory Manual*, Gassen & Lang (eds.), Verlag Chemie, Weinheim, W. Germany, 1982, pp. 97-102.*

Fritz et al., "Analysis of Synthetic Oligonucleotides," part of *Chemical & Enzymatic Synthesis of Gene Fragments: A Laboratory Manual*, Gassen & Lang (eds.), Verlag Chemie, Weinheim, W. Germany, 1982, pp. 199-223.*

McLaughlin et al., "Application of High Performance Liquid Chromatography to Oligonucleotide Purification and Separation," part of *Chemical & Enzymatic Synthesis of Gene Fragments: A Laboratory Manual*, Gassen & Lang (eds.), Verlag Chemie, Weinheim, W. Germany, 1982, pp. 177-198.*

J. McMurray, *Organic Chemistry*, Brooks/Cole Publishing Co., Monterey, CA, 1984, only p. 56 supplied.*

Thiesen et al., "Fluorescent Dye Phosphoramidite Labeling of Oligonucleotides," *Nucleic Acids Symposium Series* (1992), vol. 27, *Nineteenth Symposium on Nucleic Acids Chemistry*, IRL Press, Washinton, DC, pp. 99-100; Chemical Abstracts, 119, 191145, CAPLUS Accession No. 1993: 581145 (1993).*

Gait et al., "Synthesis of Oligodeoxyribonucleotides by Continuous . . . . ," part of Chemical & Enzymatic Synthesis of Gene Fragments: A Laboratory Manual, Gassen & Lang (eds.), Verlag Chemie, Weinheim, DE, 1982, pp. 1-42.*

Seliger et al., "Solid-Phase Synthesis of Oligonucleotides Using the Phosphite Method," part of Chemical & Enzymatic Synthesis of Gene Fragments: A Laboratory Manual, Gassen & Lang (eds.), Verlag Chemie, Weinheim, W. Germany, 1982, pp. 81-96.*

Winnacker et al., "Solid-Phase Synthesis of Oligonucleoitdes Using Phosphoramidite Method," part of Chemical & Enzymatic Synthesis of Gene Fragments: A Laboratory Manual, Gassen & Lang (eds.), Verlag Chemie, Weinheim, W. Germany, 1982, pp. 97-102.*

Fritz et al., "Analysis of Synthetic Oligonucleotides," part of Chemical & Enzymatic Synthesis of Gene Fragments: A Laboratory Manual, Gassen & Lang (eds.), Verlag Chemie, Weinheim, W. Germany, 1982, pp. 199-223.*

McLaughlin et al., "Application of High Performance Liquid Chromatography to . . . ," part of Chemical & Enzymatic Synthesis of Gene Fragments: A Laboratory Manual, Gassen & Lang (eds.), Verlag Chemie, Weinheim, W. Germany, 1982, pp. 177-198.*

J. McMurray, Organic Chemistry, Brooks/Cole Publishing Co., Monterey, CA, 1984, only p. 56 supplied.*

(Continued)

*Primary Examiner*—L. E. Crane
(74) *Attorney, Agent, or Firm*—Fish & Richardson P.C.

(57) ABSTRACT

Methods for deprotecting and derivatizing oligonucleotides that are non-covalently bound to a solid support are described. The methods include providing a plurality of oligonucleotides linked to one or more hydrophobic separation functions, wherein the plurality includes protected oligonucleotides, precipitating the plurality of oligonucleotides on a hydrophobic solid support using an organic solvent to produce non-covalently immobilized oligonucleotides, and deprotecting the immobilized oligonucleotides.

18 Claims, 4 Drawing Sheets

OTHER PUBLICATIONS

Thiesen et al., "Fluorescent Dye Phosphoramidite Labeling . . . ," *Nucleic Acids Symp. Ser.* (1992), vol. 27, 19th Symp. on Nucleic Acids Chem., IRL Press, Washington, DC, pp. 99-100; CA, 119, 191145, CAPLUS Acc. No. 1993: 581145 (1993).*

Cheng et al., "High throughput parallel synthesis of oligonucleotides with 1536 channel synthesizer," *Nucl. Acids. Res.*, 2002, 30(18—e93), pp. 1-7.

Jobs et al., "Effect of Oligonucleotide Truncation on Single-Nucleotide Distinction by Solid-Phase Hybridization," *Anal. Chem.*, 2002. 74:199-202 (WEB published on Dec. 1, 2001).

Kwiatkowski et al. "Synthesis of full-length oligonucleotides: cleavage of apurinic molecules on a novel support," *Nucl. Acids Res.*, 1996, 24(23):4632-4638, (Dec. 1996).

Kwiatkowski et al., "Inversion of in situ synthesized oligonucleotides: improved reagents for hybridization and primer extension in DNA microarrays," *Nucl. Acids Res.*, 1999, 27(24):4710-4714, (Ded. 15, 1999).

Pon, "Solid-Phase Supports for Oligonucleotide Synthesis," *Methods in Molecular Biology*, vol. 20, *Protocols for Oligonucleotides and Analogs*, Agrawal (ed.), 1993, Humana Press, Inc. Totowa, NJ, pp. 465-497.

Villadas et al., "Polymerase Chain Reaction-Temperature Gradient Gel Electrophoresis Requires the Use of High-Performance Liquid Chromatography-Purified Oligonucleotides," *Anal. Biochem.*, 2002, 300:101-103, (Jan. 1, 2002).

Fritz et al., "Analysis of Synthetic Oligodeoxyribonucleotides," *Chemical and Enzymatic Synthesis of Gene Fragments—A Laboratory Manual*, Gassen and Lang (eds.). 1982, Verlag Chemie, Weinheim, Deerfield Beach, Florida. Basel. pp. 199-224.

Gait et al., "Synthesis of Oligodeoxyribonucleotides by a Continuous Flow, Phosphotriester Method on a Kieselguhr/Polyamide Support," *Chemical and Enzymatic Synthesis of Gene Fragments—A Laboratory Manual*, Gassen and Lang (eds.), 1982, Verlag Chemie, Weinheim, Deerfield Beach, Florida, Basel, pp. 1-42.

Görtz and Seliger, "Hew Hydrophobic Protecting Groups for the Chemical Synthesis of Oligonucleotides," *Angew. Chem. Int. Ed. Engl.*, 1981, 20(8):681-682.

Kwiatkkowski et al., "Use of Reverse Phase Ion Pair Chromatography to Fractionate and Purify DNA Fragments and Monomeric Components of RNA," *Acta Chemica Scandinavica B.* 1984, 38:721-733.

Kwiatkowski et al., "The 9-(4-Octadecyloxyphenylxanthen)-9-y1-Group. A new Acid-labile Hydroxyl Protective Group and Its Application in the Preparative Reserve-phase Chromatographic Separation of Oligoribonucleotides," *Acta Chemica Scandinavica B.* 1984, 38:657-671.

McLaughlin and Krusche, "Application of High Performance Liquid Chromatography to Oligonucleotide Separation and Purification," *Chemical and Enzymatic Synthesis of Gene Fragments—A Laboratory Manual*, Gassen and Lang (eds.), 1982, Verlag Chemie, Weinheim, Deerfield Beach, Florida, Basel. pp. 177-198.

Seliger and Görtz, "Specific Separation of Products in Supported Oligonucleotide Syntheses Using the Triester Method," *Angew. Chem. Int. Ed. Engl.*, 1981, 20(8):683-684.

Seliger et al., "Solid-Phase Synthesis of Oligonucleotides Using the Phosphite Method." *Chemical and Enzymatic Synthesis of Gene Fragments—A Laboratory Manual*, Gassen and Lang (eds.), 1982, Verlag Chemie, Weinheim, Deerfield Beach, Florida, Basel, pp. 81-96.

Seliger et al., "Two New and Efficient Routes to the Preparation of Oligoribonucleotides of Defined Sequence," *Chemica Scripta*, 1983, 22:95-101.

Winnacker and Döroper, "Solid-Phase Synthesis of Oligonucleotides Using the Phosphoramidite Method," *Chemical and Enzymatic Synthesis of Gene Fragments—A Laboratory Manual*. Gassen and Lang (eds.). 1982, Verlag Chemie, Weinheim, Deerfield Beach, Florida, Basel, pp. 97-102.

Horn and Urdea, "Solid supported hydrolysis of apurinic sites in synthetic oligonucleotides for rapid and efficient purification on reverse-phase cartridges," *Nucl. Acids Res.*, 1988, 16(24):11559-11571.

Patel et al., "Improvements to solid phase phosphotriester synthesis of deoxyoligonucleotides," *Nucl. Acids Res.*, 1982, 10(18):5605-5620.

* cited by examiner

US 7,345,163 B2

```
                         SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Synthetically generated oligonucleotide

<400> SEQUENCE: 1
agagagagag agagagagag agagagagag                                         30

<210> SEQ ID NO 2
<211> LENGTH: 71
<212> TYPE: DNA
<213> ORGANISM: Artificial Sequence
<220> FEATURE:
<223> OTHER INFORMATION: Synthetically generated oligonucleotide

<400> SEQUENCE: 2
agagagagag agagagagag agagagagag agagagagag agagagagag agagagagag        60
agagagagag t                                                             71

<210> SEQ ID NO 3
<211> LENGTH: 91
<212> TYPE: DNA
<213> ORGANISM: Artificial Sequence
<220> FEATURE:
<223> OTHER INFORMATION: Synthetically generated oligonucleotide

<400> SEQUENCE: 3
agagagagag agagagagag agagagagag agagagagag agagagagag agagagagag        60
agagagagag agagagagag agagagagag t                                       91
```

```
<210> SEQ ID NO 4
<211> LENGTH: 111
<212> TYPE: DNA
<213> ORGANISM: Artificial Sequence
<220> FEATURE:
<223> OTHER INFORMATION: Synthetically generated oligonucleotide

<400> SEQUENCE: 4
agagagagag agagagagag agagagagag agagagagag agagagagag agagagagag        60
agagagagag agagagagag agagagagag agagagagag agagagagag t               111
```

PROCESS FOR SEPARATING AND DEPROTECTING OLIGONUCLEOTIDES

TECHNICAL FIELD

This invention relates to oligonucleotide separation and deprotection, and more particularly, to methods for obtaining deprotected oligonucleotides using disposable separation cartridges.

BACKGROUND

DNA-based analytical techniques, especially array based analytical methodologies, have had a tremendous impact on the development of the oligonucleotide production industry, which developed parallel synthesis techniques in order to meet the demand of the biotechnology market. Parallel synthesis allows large numbers of oligonucleotides to be synthesized on a single apparatus in a single day. This process has been optimized to such a level that most of the material, especially shorter oligonucleotides that are designed as PCR primers, can be used without any purification. In fact, many oligonucleotides are used directly in non-purified form, despite advantages that may be achieved by using purified material.

For many analytical techniques, it is desirable to use longer oligonucleotides (e.g., padlock probes of 70 to 100 nucleotides in length), as their specificity for discriminating between different targets is better then that of shorter oligonucleotides. Crude, synthetic oligonucleotides of this length are heavily contaminated by shorter fragments and need to be purified to avoid problems associated with unspecific binding (Jobs et al. *Anal. Chem.* 74 (1):199-202 (2002)). Failed couplings and/or side reactions can take place during synthesis that can produce non-full-length or incomplete oligonucleotides. In addition, acid-catalyzed depurination can occur, resulting in cleavage of the oligonucleotide backbone during oligonucleotide deprotection. As a consequence, chemical synthesis produces a population of oligonucleotides, which must be purified to obtain the desired oligonucleotide. Thus, a typical synthetic oligonucleotide reaction mixture contains three major components: full-length product, truncated fragments, and oligonucleotides that result from basic cleavage of previously depurinated oligonucleotide fragments. Full-length products may include deleted fragments (e.g., fragments with single (n–1) or two nucleotide deletions (n–2)). Further, the oligonucleotide reaction mixture may be contaminated by products with unwanted double incorporated nucleotide (n+ products), and also by fragments being incompletely or incorrectly deprotected. Impure oligonucleotides, regardless of length, may cause indistinct results, as found in analyses based on mass spectrometry or in some cases (Villadas et al. *Anal. Biochem.* 300 (1): 101-103(2002)), impure oligonucleotides can prevent obtaining any significant results.

Thus, efficient purification procedures are needed to process the large number of oligonucleotides that can be synthesized. During synthesis, a trityl moiety typically is left on the 5' end of the oligonucleotide after coupling of the last nucleotide to facilitate purification of full-length oligonucleotides. The trityl moiety, usually dimethoxytrityl (DMTr) or monomethoxytrityl (MMTr), is an acid labile protecting group that has to be finally removed. This deprotection or detritylation is usually performed in solution using 80% aqueous acetic acid or on a cartridge using an aqueous solution of 2% trifluoroacetic acid (TFA). During detritylation of an oligonucleotide using a cartridge, both the liberated oligonucleotide with free 5' OH and the newly formed trityl cation must be tightly bound to the cartridge throughout the process. Subsequently, the acid is washed out and detritylated oligonucleotide is eluted with acetonitrile and water. While this procedure appears very straightforward, the detritylation reaction

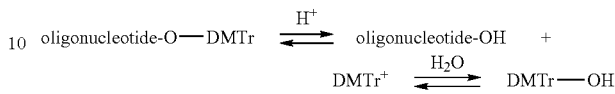

is reversible and the equilibrium constant depends on the concentration of acid and both products of deprotection. The limited mobility of oligonucleotide and trityl cation on the cartridge results in a very high effective concentration of both of these molecules. As a result, detritylation of oligonucleotides on cartridges can result in low yields of detritylated oligonucleotide (50% or less) and can be accompanied with reassociation of the trityl moiety. Non-detritylated material can be re-detritylated, although the extended deprotection in acid can result in additional apurinic sites in the oligonucleotide. Therefore, a need exists for an efficient method for detritylating oligonucleotides on cartridges.

SUMMARY

The invention is based on the discovery that oligonucleotides can be non-covalently immobilized on a solid support in a manner that renders the oligonucleotides insoluble. Consequently, the oligonucleotides can remain tightly bound to the support while hydrophobic separation functions attached to one or both ends of the oligonucleotide can be selectively removed. The methods of the invention allow oligonucleotides to be rapidly deprotected (e.g., detritylated) under mild conditions, while maximizing yield of the deprotected oligonucleotide. In addition, non-covalently immobilized oligonucleotides can be derivatized (e.g., by incorporating fluorophores) on the cartridge under non-aqueous conditions. The methods of the invention can be used for simultaneously purifying and derivatizing multiple oligonucleotides.

In one aspect, the invention features a method for deprotecting oligonucleotides. The method includes providing a plurality of oligonucleotides that includes protected oligonucleotides, wherein (i) the 5' end of each protected oligonucleotide is linked to a hydrophobic separation function or (ii) each protected oligonucleotide is linked to a pair of hydrophobic separation functions, wherein one member of the pair of hydrophobic separation functions is less hydrophobic than the other member of the pair; precipitating the plurality of oligonucleotides on a hydrophobic solid support using an organic solvent to produce non-covalently immobilized oligonucleotides; and deprotecting the immobilized oligonucleotides by (i) selectively removing the 5' separation function from the immobilized oligonucleotides or (ii) sequentially removing the pair of hydrophobic separation functions from the immobilized oligonucleotides, using a reagent dissolved in an organic solvent (e.g., dichloromethane, chloroform, acetonitrile, tetrahydrofuran, ethyl acetate, acetone, or isopropanol). Precipitating can include pre-drying the plurality of oligonucleotides on the hydrophobic solid support then washing the hydrophobic solid support with the organic solvent. The hydrophobic solid support can be provided in the form of a cartridge or a manifold containing a plurality of cartridges. The hydrophobic solid support can be polystyrene, charcoal, graphite, or silica based.

The method further can include, before precipitation, adsorbing the plurality of oligonucleotides on a hydrophobic support and eluting (i) oligonucleotides lacking the 5' hydrophobic separation function or (ii) oligonucleotides lacking any protecting group and oligonucleotides containing only the less hydrophobic separation function of the pair of hydrophobic separation functions. The method further can include eluting the deprotected oligonucleotides.

The 5' hydrophobic separation function can be a trityl moiety, a hydrophobic acetal, or a thioacetal group. The trityl moiety can be a dimethoxytrityl, trimethoxytrityl, pixyl, or monomethoxytrityl moiety. For example, the trityl moiety can be selected from the group consisting of 4-hexyloxy methoxytrityl, 4-decyloxymethoxytrityl, 4-hexadecyloxymethoxy trityl, 4-octadecyloxyphenylxanthyl, 4-4'-bis-hexyloxymethoxytrityl, 4-4'-bis-decyloxymethoxytrityl, 4-4'-bis-hexadecyloxymethoxytrityl, 4-octadecyloxytrityl, 4-hexadecyloxytrityl, 4-decyloxytrityl, and 4-hexyloxy trityl moiety. A trityl moiety can be selectively removed using a non-aqueous solution of acid (e.g., 2% trichloroacetic acid in dichloromethane).

One member of the pair of hydrophobic separation functions can be a straight chain alkyl, branched alkyl, arylalkyl, or an aryl group linked to the oligonucleotide by a linker that is removable under conditions that do not remove the other member of the pair of hydrophobic separation functions. The linker can be a siloxyl or disiloxyl function.

The oligonucleotides within the plurality can include deoxyribonucleotides or ribonucleotides, and can include a non-standard backbone (e.g., phosphorothioate, phosphorodithioate, or phosphoramido). The oligonucleotide can be a Locked Nucleic Acid (LNA). The oligonucleotide can contain one or more nucleotides linked to a functional group (e.g., an amino, thiol, phosphate, aldehyde, intercalating reagent, quencher, or a fluorophore). The functional group can be placed on either end of the oligonucleotide or placed on both ends of the oligonucleotide. The functional group can be different on each end. The 5' separation function or one member of the pair of hydrophobic separation functions can be attached to the functional group. One member of the pair of hydrophobic separation functions can be attached to a linker and the linker can be attached to the functional group.

The method further can include derivatizing the immobilized oligonucleotides using non-aqueous conditions. For example, derivatizing can include incorporating a fluorophore into the purified oligonucleotides and eluting the derivatized oligonucleotides.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
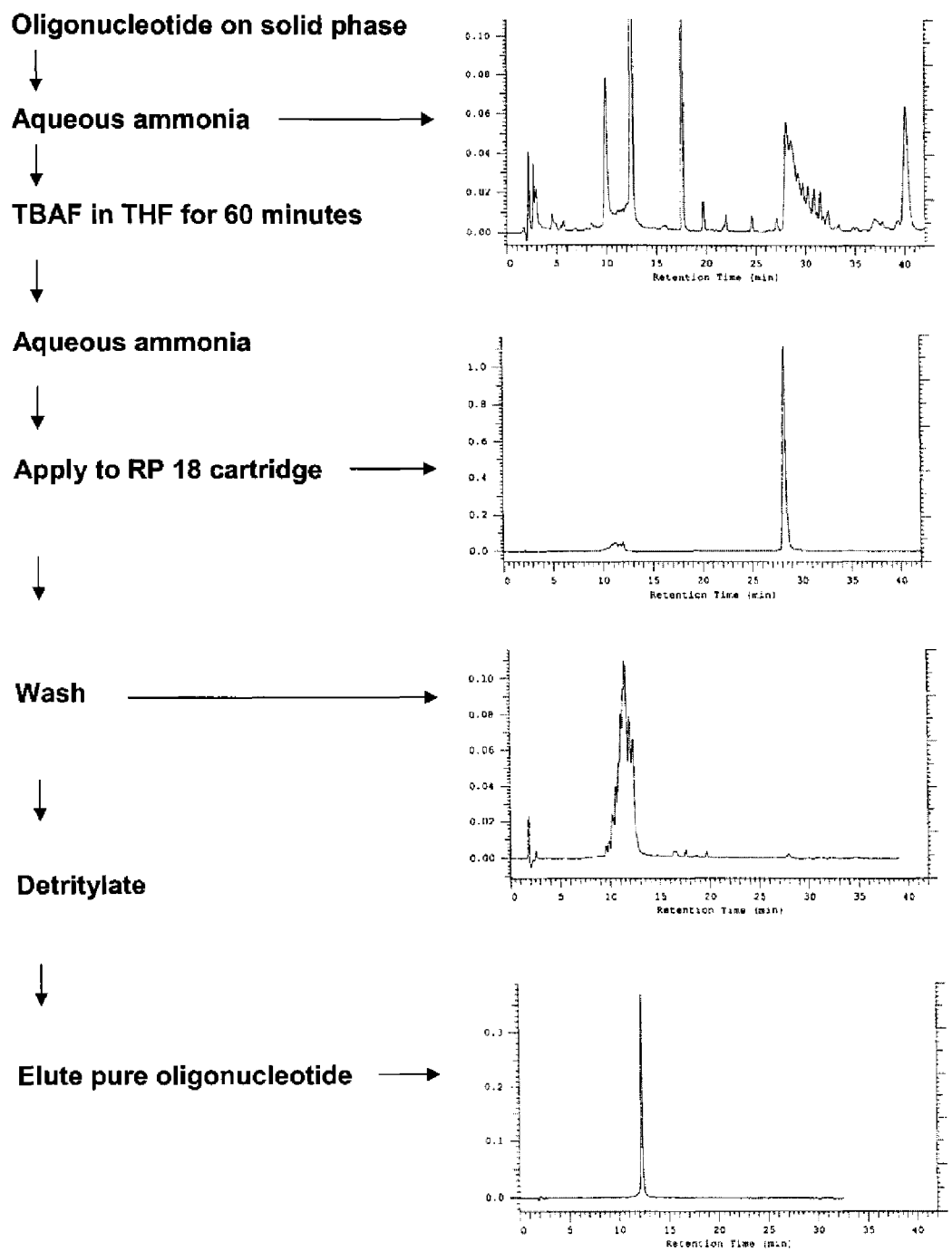
FIG. 1 is a diagram of a cartridge-based separation of a disiloxyl-linked oligonucleotide prepared on a polystyrene support.

In general, methods of the invention allow a plurality of chemically synthesized oligonucleotides, e.g., oligonucleotides synthesized on a solid support, to be separated based on hydrophobic separation functions attached to one or both ends of the oligonucleotides. Methods of the invention allow shorter fragments resulting from depurination and subsequent cleavage of the oligonucleotide material to be separated from full-length oligonucleotides. This extends the length of material that can be efficiently and practically separated by chromatography to the current limit of DNA synthesis. In some embodiments, an oligonucleotide can be non-covalently immobilized on a solid support in a manner such that the oligonucleotide is insoluble and a 5' hydrophobic separation function (e.g., 5' protecting group) can be removed and the oligonucleotide can be derivatized. In other embodiments, the oligonucleotide is attached to a pair of hydrophobic separation functions, wherein one member of the pair of hydrophobic separation functions is less hydrophobic than the other member of the pair. Methods of the invention can be used for high throughput, multiple separations of oligonucleotides on disposable cartridges (reversed-phase cartridges).

Oligonucleotides

As used herein, the term "oligonucleotide" includes oligomers of ribonucleotides and deoxyribonucleotides that have a 3'-5' phosphodiester backbone, as well as oligomers of ribonucleotides and deoxyribonucleotides with backbone structures differing from the standard 3'-5' phosphodiester linkage (e.g., peptide-nucleic acids (PNAs), methyl phosphonate, phosphorothioate, phosphorodithioate, or phosphoramido linkages). The term "oligonucleotide" also includes oligomers that contain non-standard base moieties such as inosine or nubularine, modified base moieties, modified sugar moieties, and combinations of such moieties. For example, the nitrogenous bases or sugar moieties can be modified to include reactive functionality (e.g., C5 propyne, halide, or biotin) and labels (e.g. radioactive, luminescent, electroluminescent, visible, near-IR, and fluorescent). An additional modification of the sugar moiety includes the addition of a methylene linker that connects the 2'-O position to the 4'-C position of the furanose ring. This modification is referred to as a locked nucleic acid (LNA); nucleic acids containing one or more LNA modifications are called LNA.

Methods for synthesizing oligonucleotides, including oligonucleotides containing non-standard bases, are known in the art. For example, oligonucleotides can be assembled by the β cyanoethyl phosphoramidite method. See, for example, "Oligonucleotide Synthesis: A Practical Approach," ed. M. J. Gait, IRL Press, 1984, WO92/09615; and WO98/08857 for a description of oligonucleotide synthesis methods. Automated oligonucleotide synthesizer machines can be used to produce oligonucleotides. Such synthesizers are known and are available from a variety of companies including Applied Biosystems and Amersham Pharmacia Biotech.

Oligonucleotide syntheses typically utilize a solid support to which one or more protected nucleotides are attached via a linker to the nucleotide's 3'-oxygen. A linker refers to any molecule containing a chain of atoms, e.g., carbon, nitrogen, oxygen, etc., that is hydrolytically stable and serves to link the molecules to be synthesized on the support with the support. The linker is usually attached to the support via a covalent bond before synthesis on the support starts, and provides one or more sites for attachment of precursors of the molecules to be synthesized. It is to be understood that, at times, linkers include one or more nucleotides, e.g., polyT, that are not part of the finished full-length oligonucleotide. Nucleotides that are part of the linker, but are not part of the finished full-length oligonucleotide, are not considered to be the 3'-end of an oligonucleotide. Disiloxyl-containing linkers (e.g., a tetraisopropyl disiloxyl function linked directly to the 3' hydroxyl of the oligonucleotide) are particularly useful and can be created using the methods provided in Kwiatkowski et al., *Nucleic Acids Res.*, 24:4632-4638 (1996); Kwiatkowski et al., *Nucleic Acids Res.*, 27(24):4710-14 (1999); or WO 98/08857. It is noted that functional groups (e.g., amino, thiol, phosphate, aldehyde, intercalating reagents, quencher, or fluorophores) can be attached to the linker.

As additional nucleotide monomers are added successively, the resulting oligonucleotide is extended in a 3' to 5'-end direction. Once an oligonucleotide has reached the desired length, techniques described in the above publications can be used to partially deprotect the oligonucleotide, cleave apurinic sites, and remove any shorter fragments resulting from the cleavage. Oligonucleotides that remain bound to the synthesis support then can be removed from the support. In the case of a disiloxyl linker, a reagent that disrupts the silica-oxygen bond can be used to cleave the oligonucleotide from the support.

Separation Functions

Typically, a plurality of oligonucleotides that contains protected oligonucleotides is used in methods of the invention. As used herein, a protected nucleotide refers to an oligonucleotide having a hydrophobic separation function attached to its 5' end or a pair of hydrophobic separation functions attached to the oligonucleotide, with one member of the pair attached to the 5' end and the other member attached to the 3' end of the oligonucleotide. If a pair of hydrophobic separation functions is attached to the oligonucleotide, one member of the pair of hydrophobic separation functions is less hydrophobic than the other member. In one embodiment, the 3' separation function can have a substantially higher hydrophobicity than the 5' separation function. In other embodiments, the 5' separation function can have a substantially higher hydrophobicity.

Separation functions attached to the 3' end of the oligonucleotide can be a component of the linker between the solid support and the first nucleotide, i.e., 3'-end, of the oligonucleotide. The separation function on the 3' end of the oligonucleotide typically is stable under treatment in aqueous ammonia so the separation function will not be cleaved from the oligonucleotide when the oligonucleotide is released from the solid support. Suitable 3' separation functions include, for example, straight chain alkyls, branched alkyls, arylalkyls, or aryl groups. Linear or branched diols such as 1,10-decanediol or other hydrophobic diols are particularly useful hydrophobic separation functions.

A 5' separation function can be introduced together with the 5' terminal nucleotide building block as a terminal, appropriately derivatized phosphoramidite is added to the oligomer during synthesis. The term "building block" includes both terminal nucleotides and chemical moieties for introducing terminal functional groups like phosphate, amine, thiol, hydrazo, aldehydo or aminooxyl group. Suitable separation functions for the 5' end of oligonucleotide are not limited to the standard dimethoxytrityl (DMTr), pixyl (Px) or monomethoxytrityl (MMTr) groups, but include all types of acid labile protecting groups. Of particular importance are trityl (Tr), trimethoxytrityl (TMTr), methoxypixyl (MPx), and other groups that introduce an additional hydrophobicity to the oligonucleotide. The latter can be selected among 4-hexyloxy methoxytrityl (C6MTr), 4-decyloxymethoxytrityl (C10MTr), 4-hexadecyloxymethoxy trityl (C16MTr), 4-octadecyloxyphenylxanthyl (C18Px), 4-4'-bis-hexyloxymethoxytrityl (bisC6Tr), 4-4-bis-decyloxymethoxytrityl (bisC10MTr), and 4-4'-bis-hexadecyloxymethoxytrityl (bisC16MT), 4-octadecyloxytrityl (C18Tr), 4-hexadecyloxytrityl (C16Tr), 4-decyloxytrityl (C10Tr), and 4-hexyloxy trityl (C6Tr). See, also U.S. Pat. No. 5,892,007 for examples of other highly hydrophobic trityl groups. These very hydrophobic functions are of value for separating relatively long oligonucleotides, where the contribution of the usual dimethoxytrityl group may be not sufficient for quantitative and loss-free anchoring of the tritylated molecules on the support. Different types of substituted trityl groups also can be introduced on the 5' position in the synthetic oligonucleotides in a process of trityl exchange as described in U.S. Pat. No. 5,319,079. Hydrophobic acetal or thioacetal groups also are useful 5' functions.

Separation functions with strong hydrophobicity are useful for synthesizing and purifying double-labeled oligonucleotides (e.g., taqman-probes and molecular beacons), which are labeled with a different dye on each end of the oligonucleotide. Such probes must be very pure in order for efficient quenching of the dyes fluorescence. To achieve a satisfactory purity, probes of this kind are often prepared in a several step process that is followed at each step by an extensive chromatographic purification. The need for such a lengthy procedure is reflected in the high prices of the commercial double-labeled probes. Typical dyes used for preparing double-labeled probes have substantial hydrophobic properties; thus, using a standard DMTr group as a 5' separation function would result in a mixture that is very hard to separate on a HPLC and impossible to resolve on a cartridge. Replacing the DMTr group with a C18Px or C18Tr function that is more hydrophobic than DMTr, however, negates the hydrophobic contribution from both dyes and allows the double-labeled probe to be separated according to methods of the invention.

Adsorbing to Hydrophobic Supports

After an oligonucleotide has been released from the support on which it was synthesized, the oligonucleotide can be adsorbed on a hydrophobic support. Typically, the hydrophobic support is composed of hydrocarbon chains ranging from 4 to 24 carbons (e.g., 8 to 18 carbons) in length that are chemically bonded to a support material, such as silica, charcoal, graphite, or polystyrene-based particles. The hydrocarbon chains can be branched and can have one or more aromatic substitutions. For example, a C18 chain can be bonded to a silica-based particle to form a useful hydrophobic support. Copolymers of styrene and divinylbenzene are common support materials that are relatively inexpensive and inert to many reagents and solvents. Resistance to alkaline ammonia solutions and to TBAF makes this material particularly useful. While silica-based materials are not as resistant to reagents and solvents as styrene based supports, the short contact time between any harmful reagents and silica-based supports, as well as the possible deactivation of some reagents by their dilution with water, allows the supports to be useful. In fact, small HPLC columns filled by RP 18 silica and pre-treated by 10% aq. ammonia or 0.1 M TBAF in water, did not show any substantial difference in separation of a model oligonucleotide reaction mixture compared to the untreated column.

Additional useful supports include zirconium oxide-based materials, which have a low susceptibility for alkaline degradation, or supports based on active carbon, which are completely resistant to alkaline degradation.

Typically, the hydrophobic support is provided in the form of a cartridge or a manifold containing a plurality of cartridges (e.g., a cartridge plate). Disposable cartridges are reliable and non-expensive, and allow for scaling up either the number of simultaneous separations or the amount of isolated material. Systems containing a variety of elements (e.g., valves, pumps, injection units and fraction collectors) and cartridges can be configured to automate the separation of oligonucleotides. Cartridges can be run in sequential or parallel fashion depending on the isolation order preferred for particular oligonucleotides. Processes for separating the oligonucleotides can be automated (e.g., using a robotic system to handle all samples and solvents). To avoid problems associated with differences in cartridge performances and to decrease processing time, the manifold or other platform can be coupled to, and driven by, a vacuum system, which allows all cartridges to be dried after addition of each reagent or eluent.

To avoid substantial losses of product when adsorbing an oligonucleotide to a hydrophobic support, the oligonucleotide can be pre-treated to reach an optimal form for interaction with the solid phase. This can be achieved by using a buffer containing a hydrophobic counterion that renders the oligonucleotide more hydrophobic. The degree of hydrophobicity introduced to the oligonucleotide can be controlled by choosing a substance from the group of tri- or tetra- methyl, ethyl, propyl, butyl, and pentylammonium salts. Tertiary and quaternary ammonium salts are particularly useful. Practically, it is advantageous to use salts that are easily volatile, such as carbonates or acetates. Another consideration is the tendency of oligonucleotides possessing strongly hydrophobic separation functions to aggregate into structures that do not penetrate into the fine pores of the support, but rather, run straight through the cartridge. To break these aggregates, the salt concentration can be increased to a relatively high level, and an organic solvent like ethanol, acetonitrile, or dimethylformamide (DMF) can be used to solvatize the hydrophobic structures.

Once the oligonucleotide is adsorbed to the hydrophobic support, oligonucleotides lacking the 5' hydrophobic separation function can be eluted. In the case of an oligonucleotide linked to a pair of hydrophobic separation functions, oligonucleotides lacking any protecting group and oligonucleotides containing only the less hydrophobic separation function are eluted. For example, when the 3' separation function has higher hydrophobicity, oligonucleotides that lack any separation function can be eluted as well as oligonucleotides only having the 5' separation function. If the 5' separation function has higher hydrophobicity, oligonucleotides that lack any separation function can be eluted as well as oligonucleotides only having the 3' separation function.

To eliminate oligonucleotides lacking the 5' hydrophobic separation function (e.g., a trityl function), an eluting solvent composed of triethylammonium acetate and 10-20% acetonitrile can be used to effectively wash out the less-hydrophobic oligonucleotides. While oligonucleotide fragments that appear as a result of depurination and subsequent cleavage of the depurinated chain are more hydrophobic then the full-length material and difficult to fractionate, the present invention allows these fragments to be efficiently washed away prior to the actual cartridge separation, or to be selectively eliminated on cartridges using systems operating with two separation functions.

Precipitating Oligonucleotides on Hydrophobic Solid Supports

After eliminating all shorter fragments, the remaining product can be simple eluted from the cartridge and then detritylated after evaporation of the volatile matters. This procedure, however, requires an additional evaporation of acid, and usually a desalting stage. In the present invention, the separation function on the 5' end of the oligonucleotide, or the pair of hydrophobic separation functions on the oligonucleotide, can be eliminated while the oligonucleotide is attached to a cartridge.

As described herein, the oligonucleotides can be precipitated on a cartridge in an organic solvent, and the separation functions subsequently can be removed. The oligonucleotide can remain tightly bound to the support while the 5' separation function (e.g., trityl moiety) can be selectively removed or while the 5' and 3' separation functions are sequentially removed. Thus, oligonucleotides can be rapidly deprotected (e.g., detritylated) under mild conditions, while maximizing yield of the deprotected oligonucleotide. As used herein, the term "precipitated" refers to the formation of insoluble, dehydrated material on the support surface. For example, an oligonucleotide can be precipitated on a cartridge by drying by air and then flushing with acetonitrile. Oligonucleotides treated in such a manner remain tightly bound to the cartridge and no oligonucleotide loss was observed, even in the acetonitrile front fraction. See, Example 1. Oligonucleotides can be precipitated with organic solvents such as acetonitrile or other organic solvent such as dichloromethane, chloroform, tetrahydrofuran, ethyl acetate, acetone, or isopropanol. It is noted that the organic solvent may contain a small percentage of water and still be suitable for use in the present invention.

Once the oligonucleotide is non-covalently immobilized on the solid support, the 5' separation tag can be removed using a non-aqueous solution of acid (e.g., 2% trichloroacetic acid (TCA) in dichloromethane). For example, when a dichloromethane solution of 2% TCA was applied to a cartridge containing an oligonucleotide protected with a DMTr moiety, a visible orange band of DMTr cation rapidly formed, and was easily washed out from the cartridge. As described herein, 96 oligonucleotides can be separated on a C18-silica cartridge plate in less than 30 minutes, which is faster than other commercially available systems that can take up to 4 hours to separate the oligonucleotides. Thus, in the present method, the trityl moiety is eliminated from the cartridge, which pushes the detritylation reaction to completion. Excess acid can be removed by washing with an organic solvent (e.g., acetonitrile), and the final product can be eluted from the cartridge by an eluent containing acetonitrile or other organic solvent. Compositions containing 40% acetonitrile were capable of eluting all oligonucleotide containing material. If desired, any remaining non-deprotected oligonucleotide can be detected in a separate analytical HPLC run. As described herein, only traces of tritylated starting material (usually much less than 5%) were observed, showing that the present detritylation procedure is essentially quantitative.

When a 5'-aminoalkyl oligonucleotide, protected by a MMTr group, was adsorbed, precipitated, and detritylated as described above, a yellow band of MMTr cation was formed immediately, and was easily washed out from the cartridge. The entire detritylation process was performed in less then 195 seconds with a quantitative yield. In this same time frame, 2% TFA resulted in only 8.4% conversion to the detritylated material. By applying first order kinetics, it was estimated that it would take 2% TFA 140 minutes for 99% detritylation. The actual acid concentration of 2% v/v TFA corresponds to 0.26 M and 2% w/v TCA is only 0.12 M. Thus, it is surprising that 2% TCA had a 120-fold difference in reactivity, despite the fact that the TFA solution was about 20 times more acidic then TCA.

In the case of an oligonucleotide linked to a pair of separation functions, where the 3' separation function has a higher hydrophobicity than the 5' separation function, the linker can be cleaved and oligonucleotides lacking any hydrophobic function can be eluted. The remaining material can be reprecipitated on the cartridge using an organic solvent, and the 5' separation function can be removed and pure, deprotected product can be eluted as discussed above. When the 5' separation function has a higher hydrophobicity than the 3' separation function, the 5' separation function can be removed as discussed above and fragments lacking any hydrophobic function can be eluted. Remaining material can be reprecipitated on the cartridge with an organic solvent, the linker can be cleaved, and pure, deprotected product can be eluted.

Derivatizing Oligonucleotides

Once the oligonucleotides possessing reactive functionalities are non-covalently immobilized on a solid support, the oligonucleotides can be derivitized in a selected organic solvent and with reagents that are otherwise reactive with water. Non-limiting examples of non-aqueous solvents that can be used include pyridine, dimethyldormamide, dimethylsulfoxide, triethylamine, acetone, acetonitrile, and dichloromethane. Non-limiting examples of reagents that are reactive with water include acid chlorides, acid anhydrides, mixed anhydrides, and acids used with different activating reagents. Further, many functional groups are delivered as active esters, many of which are costly and need to be used with maximal efficiency. Thus, in the present method, active esters can be used to derivatize oligonucleotides without undergoing hydrolysis. One or more nucleotides of an oligonucleotide can be derivatized by incorporating a functional group such as an amino, thiol, phosphate, aldehyde, intercalating reagent, quencher, fluorophore, or moieties that allow an oligonucleotide to penetrate cell membranes. In some embodiments, a functional group is placed on either end of the oligonucleotide. In other embodiments, a functional group is placed on both ends of the oligonucleotide. The functional group can be different on each end of the oligonucleotide.

The invention will be further described in the following examples, which do not limit the scope of the invention described in the claims.

EXAMPLES

Reagents and Analytic and Preparative Methods Used in the Examples

Unless indicated otherwise, the following reagents and methods were used in the Examples that follow this methods section.

5'-O-(4,4'-dimethoxy)trityl thymidylyl 3'-O-(1,1,3,3-tetraisopropyl-disiloxyl-3)-(1-O-3,6,9-trioxa)undecan-11-ol and its phosphoramidite derivative were prepared according to WO 98/08857. Commercially available CPG (1000 Å; CPG Inc., Fairfield; or Applied Biosystems, Foster City, Calif.) was aminated with methods similar to those described by Pon, R T, "Chapter 19 Solid-phase Supports for Oligonucleotide Synthesis," *Methods in Molecular Biology Vol. 20 Protocols for Oligonucleotides and Analogs*, 465-497, Ed. S. Agrawal, Humana Press Inc., Towata, N.J. (1993). The hydroxyl CPG was obtained by reacting aminoderivatized CPG with gamma-butyrolactone in pyridine. All commercial chemicals were of synthesis quality and were used without further purification.

Oligonucleotide syntheses were performed on an ABI 394 DNA Synthesizer or on a MultiSyn, a 1536 channel oligonucleotide synthesizer developed at Institute of Biomedical Sciences, Academia Sinica, Taipei, Taiwan (Cheng et al. *Nucleic Acids Res.* in press (2002)). All couplings were performed using amidites protected by benzoyl (dA, dC) and/or isobutyryl (dG) groups at the exocyclic amine functions, under conditions recommended for 0.2 µmol scale synthesis or smaller. If demanded, the last nucleoside phosphoramidite was substituted with a nucleoside phosphoramidite derivatized with another 5'protecting group, or the final dimethoxytrityl (DMTr) groups were exchanged by other trityl derivatives according to the trityl exchange method (see U.S. Pat. No. 5,319,079).

Analytical liquid chromatography of ammonia deprotected oligonucleotides was performed on a Hitachi-Merck La Chrom HPLC system, equipped with a LiChrosorb RP 18 (5 µm) column, diode array detector, using a 40 minutes linear gradient of solvent A:acetonitrile ("MeCN") 5% v/v in 0.1 M triethylammonium acetate ("TEAA"), pH 7.0, and solvent B:acetonitrile 80% v/v in 0.1 M TEAA, pH 7.0. Capillary electrophoresis (CE) analyses were run on a Beckman system using a ssDNA 100-R capillary unit (capillary length 30 cm).

Example 1

Cartridge-based Separation of a Disiloxyl-linked Oligonucleotide Prepared on a Polystyrene Support An oligonucleotide (26 mer) was synthesized on an aminomethyl polystyrene support (ABI) according to the following procedure (see also FIG. 1): a cassette containing 0.2 mmol of aminomethylpolystyrene (19 mmol/g) was placed on an ABI 394 DNA synthesizer, and three consecutive couplings of T amidite were performed. These couplings were followed by a single addition of a disiloxyl dG amidite to achieve a linker and a starting point for oligonucleotide synthesis. The rest of the sequence was synthesized according to standard procedures. The product synthesized on the solid support was treated with concentrated aqueous ammonia using trityl-on methodology, but in this case, the product covalently bound to the solid phase support was taken to the further procedure instead of the ammonia washes.

The support was transferred to a Soersted tube, and treated with concentrated aqueous ammonia at 55° C. for 12 hours. After centrifugation, the ammonia supernatant was combined with the previous ammonia washes and analyzed on reverse phase HPLC to reveal the presence of all of the shorter, trityl containing fragments, that resulted upon basic cleavage of apurinic sites. The residual support was dried by washing with acetonitrile and treated with tetrabutylammonium fluoride (0.2 ml, 1 M in THF) for 2 hours at room temperature. Volatile matters were evaporated in vacuum and the binding buffer (1 M NaCl+5% DMF in water) (1.0 ml) was added to the residual suspension. The clear supernatant was applied to a cartridge prepared from 130 mg of hydrophobic, polystyrene based support and residual fragments lacking trityl function were eluted with buffer composed of 20% acetonitrile and 0.1 M triethyl ammonium acetate (TEAA) to produce a single, full-length product that remains on the cartridge, as indicated by HPLC analyses. Air was passed through the cartridge to remove traces of water, followed by pure acetonitrile (2×1,0 ml) to precipitate the material present on the cartridge. The excess of acetonitrile was removed by flow of air and the detritylating mixture composed of 2% trichloracetic acid (TCA) in dichloromethane was added, resulting in immediate formation of an orange band on the cartridge. This band of cleaved DMTr cation was quickly eluted out from the cartridge so the whole cleavage and removal procedure was over in less than 2 minutes. The cartridge containing the residual acid was washed with pure acetonitrile, dried, and the final pure product eluted out using 40% acetonitrile containing 0.1 M TEAA. Alternatively, the dried cartridge could be washed with pure water and then eluted with 50% acetonitrile in water. The later method produces oligonucleotide free of excess salts.

Example 2

Figure 2:
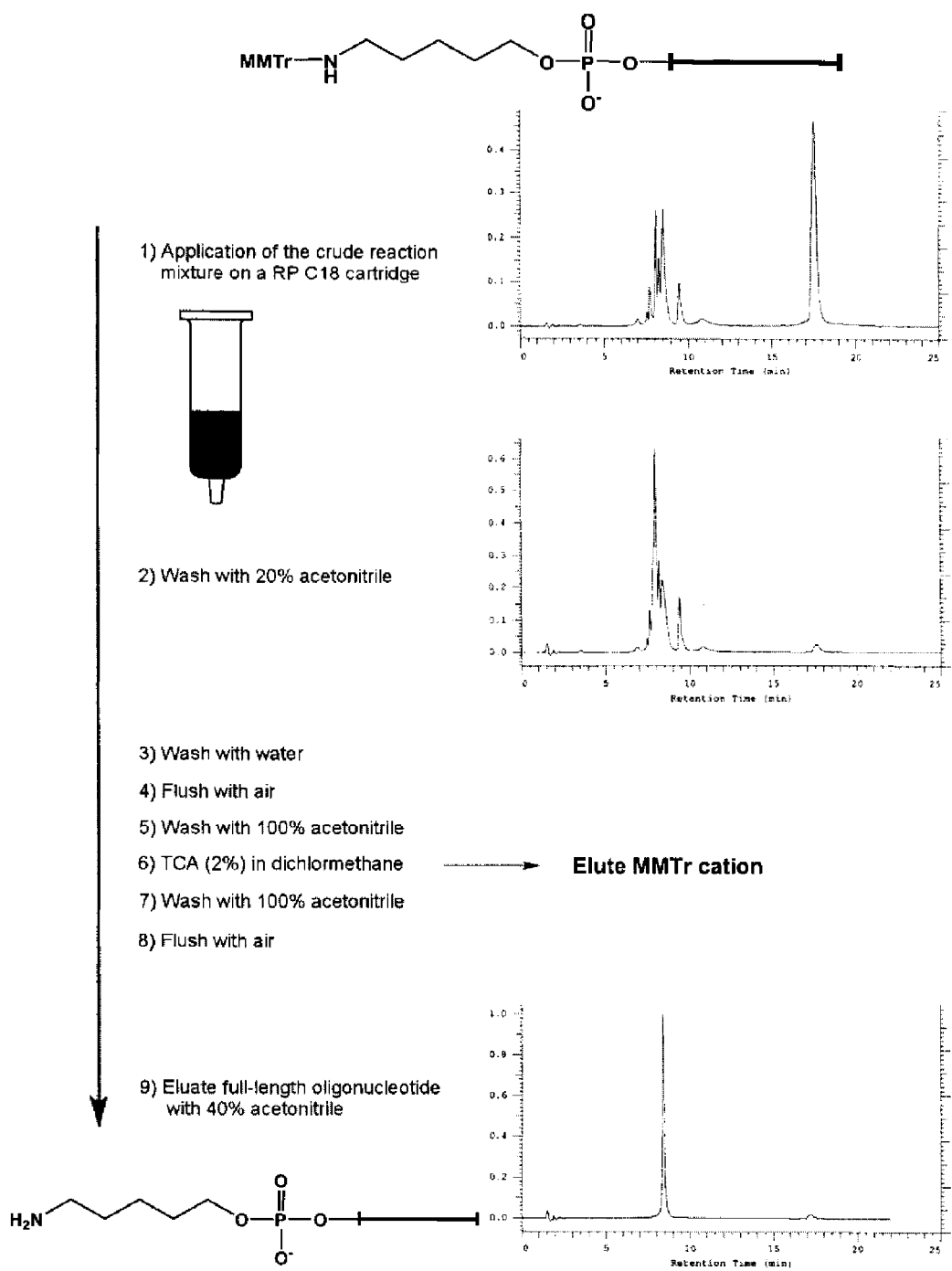
FIG. 2 is a presentation of a cartridge-based separation and deprotection of MMTr-NH-labeled oligonucleotide.

Removal of MMTr Group from the 5'-amino Derivatized Oligonucleotides:

An oligonucleotide containing MMTr-NH-C5 function was prepared according to standard procedures for synthetic oligonucleotides. The deprotected material was subjected to the cartridge purification and on-cartridge trityl removal, essentially as described in the Example 1, but using slightly longer time for trityl removal (also see FIG. 2). The yellow MMTr cation was removed from the cartridge in 4 minutes, which was enough time for the quantitative detritylation of the product, as it was found from a separate HPLC analysis.

It was found in an analogous experiment, but using 2% aqueous trifluoroacetic acid (TFA), that less then 10% of the product could be detritylated under the same time.

Example 3

Figure 3:
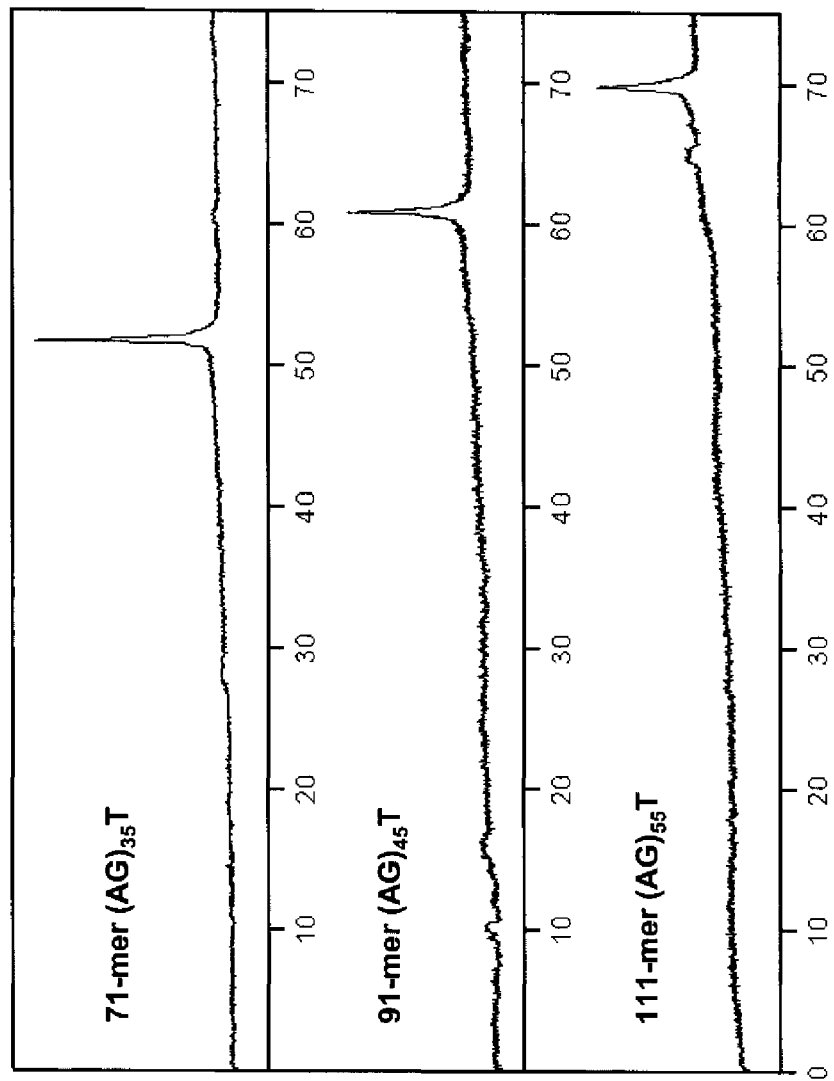
FIG. 3 shows selected capillary electrophoresis runs of cartridge purified oligonucleotides.

Double On-cartridge Oligonucleotide Deprotection for the Purification of Molecules with Two Separation Functions:

An oligonucleotide was constructed on a standard CPG support containing a thymidine residue linked to the support via a simple ester linkage. To this starting residue, three consecutive couplings of a hydrophobic building block and a single coupling of disiloxyl dG amidite were performed. The hydrophobic building group used in the present experiment was a phosphoramidite derivative of 1, 12-dodecanediol (commercially available from Glen Research). The rest of oligonucleotide contained standard nucleotides to obtain a 30-mer $(AG)_{15}$ (SEQ ID NO:1), 71-mer $(AG)_{35}T$ (SEQ ID NO:2), 91-mer $(AG)_{45}T$ (SEQ ID NO:3), or 111-mer $(AG)_{55}T$ (SEQ ID NO:4). The trityl-on synthesized material was treated with ammonia, and the partially deprotected oligonucleotide was collected in ammonia after its cleavage from the support. Heating at 55° C. for 12 hours, which eliminates all base labile protecting groups, yielded a mixture containing four major group of compounds; 1) full-length oligonucleotides containing both 5' DMTr and the 3'-hydrophobic function, 2) truncated fragments and 3'-parts of depurinated oligonucleotides having the 3'-hydrophobic moiety, 3) tritylated fragments of depurinated and cleaved oligonucleotides, and 4) fragments lacking any of the hydrophobic functions, formed as a result of double depurination/cleavage of the synthesized material. The above mixture was applied on the polystyrene cartridge and materials belonging to group 3 and 4 were washed out with 35% acetonitrile+0.1 M TEAA, then the cartridge was washed with water, dried with air, and the adsorbed oligonucleotides were precipitated with acetonitrile followed by a single wash with pure tetrahydrofuran (THF). The hydrophobic 3' separation function was then released by on-cartridge cleavage of disiloxyl function using 1 M TBAF in THF (0.4 ml) for 2 hours at room temperature. The cartridge was subsequently treated using the following steps: a) THF, b) acetonitrile, c) air drying, d) water, e) 20% acetonitrile+ 0.1 M TEAA, f) water, g) air drying, and h) pure acetonitrile. At this stage, the cartridge contained only precipitated, tritylated full-length components, which were detritylated with 2% TAC and finally eluted as described in Example 1. The isolated and evaporated material was analyzed by reverse phase HPLC and CE. FIG. 3 provides representative CE analyses of the cartridge-purified oligonucleotides.

Example 4

Figure 4:
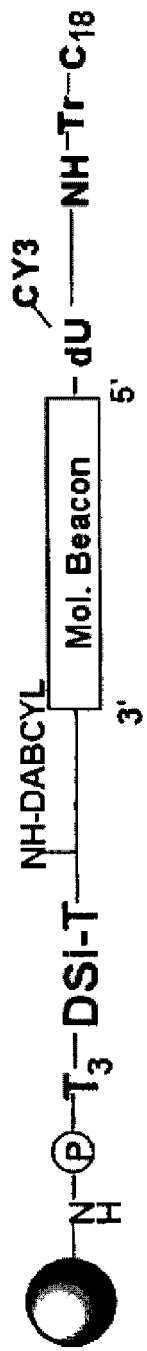
FIG. 4 is a synthetic scheme for a double-labeled oligonucleotide (molecular beacon).
Figure 4:
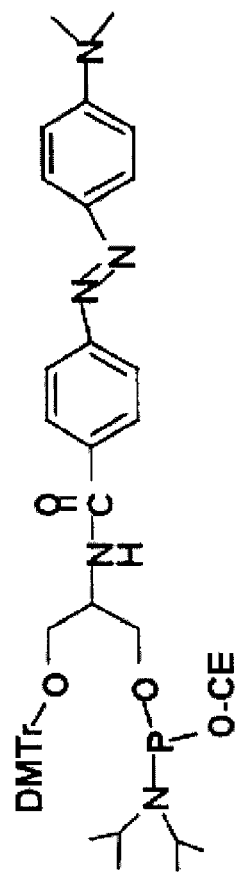
Figure 4:
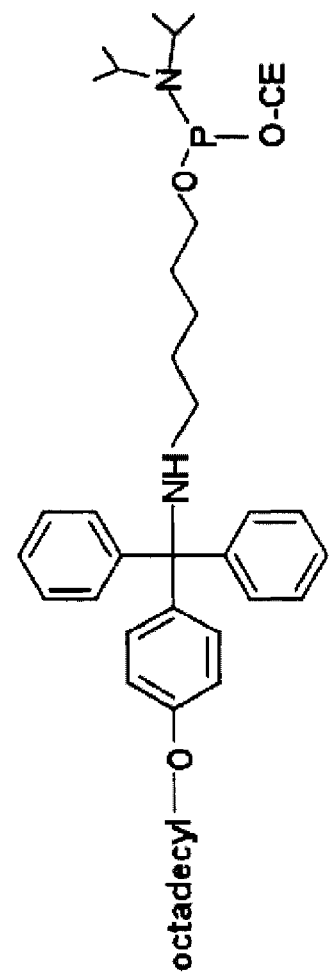

Synthesis and Separation of Double-labeled Molecular Probes:

1) A trifunctional building block (FIG. 4) containing the DABCYL (quencher) moiety, DMTr-O extendable part, and phosphoramidate function was prepared starting from DABCYL-NHS ester (succinimidyl ester) (Molecular Probes) and 2-amino-1,3-propandiol (Aldrich). The isolated amido 1,3-diol was tritylated and phosphitylated according to standard literature procedures. Functionally identical building blocks can be purchased for instance from Chem Genes Corporation.

2a) Octadecyloxyphenyl bromide was obtained from octadecylbromide and 4-brom phenol according to published procedure. This compound was purified by distillation in high vacuum.

2b) Octadecyloxytriphenylmethane ($C_{18}$ Tr-OH) was prepared in a Grignard procedure starting from octadecyloxyphenyl bromide and magnesium in dry THF. Benzophenone was added to the metalorganic compound and the product was hydrolyzed with 2 M HCl. The worked-up reaction mixture was dried, evaporated, and the pure product crystallized from toluene. The trityl alcohol was converted to the trityl chloride by treatment with an excess of acetylchloride.

2c) 1-Amino-pentanol-5 was silanized with trimethylchlorosilane in pyridine and tritylated with the obtained $C_{18}$ Tr chloride to form $C_{18}$ Tr—NH—$C_5$—OH. The isolated material was subsequently phosphitylated to form the building block (FIG. 4), for introduction of separation function with an enhanced hydrophobicity. The above procedure was performed analogously to the synthesis of commercially accessible MMTr-NH-derivative.

3) An aminomethyl polystyrene support was reacted with three standard thymidine residues followed by one disiloxyl modified thymidine block. The synthesis of a molecular beacon was started by single coupling of the quencher amidite, followed by synthesis of a DNA probe, a 38-mer having 6 bases at each end that are complementary to each other. The synthesis was accomplished by adding a fluorophore unit (CY3, Amersham Biosciences) and a C18 Tr derivative as a separation function. The synthesized material was deprotected by aqueous ammonia and the solid support was washed several times with acetonitrile /water 1:1 to eliminate all depurinated and cleaved molecules. The remaining material was cleaved from the support as described above, and applied to the separation cartridge. Extensive washes using 40% acetonitrile+0.1 M TEAA were used to remove all traces of both truncated sequences and 3'-end parts of depurinated sequences. The remaining material was precipitated and detritylated on the cartridge as described in Example 1. The purity of the finally eluted material was tested both on HPLC and CE, which showed only the presence of double-labeled, full-length molecular beacon.

Example 5

On-cartridge Oligonucleotide Derivatization

A 26-mer oligonucleotide, labeled at 5'-end by a MMTr-NH-C5- group was synthesized, purified, and detritylated on a cartridge as described in Example 2. Instead of eluting the product, however, the acetonitrile washed cartridge with the precipitated 5' amino oligonucleotide was treated with an excess of fluorescein isothiocyanate dissolved in a mixture composed of acetonitrile:DMF:pyridine 7:2:1, for 6 hours at room temperature. Unreacted reagent was washed out using the solvent of the same composition, followed by washing with acetonitrile and air drying. The finally eluted product was analyzed by HPLC to show the conversion of the starting material to the 5'-fluorescein labeled product.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for deprotecting oligonucleotides, said method comprising:
   a) providing a plurality of oligonucleotides, wherein at least some of said oligonucleotides are each linked to a single trityl or substituted trityl moiety hydrophobic separation function at the 5' end;
   b) precipitating said plurality of oligonucleotides on a hydrophobic solid support by (i) adsorbing said plurality of oligonucleotides onto said hydrophobic solid support, (ii) drying said adsorbate on said hydrophobic solid support, and (iii) contacting said dried adsorbate on said hydrophobic solid support with an organic solvent; and
   c) removing said 5' trityl or substituted trityl moiety hydrophobic separation function from said precipitated oligonucleotides by contact with a non-aqueous solution of acid in order to deprotect said oligonucleotides.

2. The method of claim 1, said method further comprising eluting said acid-contacted oligonucleotides.

3. The method of claim 1, wherein said organic solvent is dichloromethane, chloroform, acetonitrile, tetrahydrofuran, ethyl acetate, acetone, or isopropanol.

4. The method of claim 1, wherein said non-aqueous solution of acid is 2% trichloroacetic acid in dichloromethane.

5. The method of claim 1, wherein said hydrophobic solid support is provided in the form of a cartridge or a manifold, said manifold containing a plurality of cartridges.

6. The method of claim 1, wherein said hydrophobic solid support is polystyrene, charcoal, graphite, or silica based.

7. The method of claim 1, wherein said substituted trityl moiety is a dimethoxytrityl, trimethoxytrityl, pixyl, or monomethoxytrityl moiety.

8. The method of claim 1, wherein said substituted trityl moiety is selected from the group consisting of 4-hexyloxy methoxytrityl, 4-decyloxymethoxytrityl, 4-hexadecyloxymethoxy trityl, 4-octadecyloxyphenylxanthyl, 4-4'-bis-hexyloxymethoxytrityl, 4-4'-bis-decyloxymethoxytrityl, 4-4'-bis-hexyloxymethoxytrityl, 4-octadecyloxytrityl, 4-hexadecyloxytrityl, 4-decyloxytrityl, and 4-hexyloxy trityl moiety.

9. The method of claim 1, wherein the oligonucleotides within said plurality contain deoxyribonucleotides or ribonucleotides.

10. The method of claim 9, wherein the oligonucleotides contain a non-standard backbone.

11. The method of claim 10, wherein a component of said non-standard backbone is a phosphorothioate, phosphorodithioate, or phosphoramido linkage.

12. The method of claim 9, wherein the oligonucleotides are Locked Nucleic Acids (LNAs).

13. The method of claim 9, wherein the oligonucleotides comprise an amino group at the 5' end.

14. The method of claim 13, wherein said 5' trityl or substituted trityl moiety hydrophobic separation function is attached to said amino group.

15. The method of claim 13, wherein said 5' trityl or substituted trityl moiety hydrophobic separation function is attached to a linker and said linker is attached to said amino group.

16. The method of claim 1, said method further comprising, in step (b), derivatizing said immobilized oligonucleotides by incorporating a fluorophore at the 5' end by (iv) contacting said oligonucleotides with a fluorophore in a non-aqueous solvent, and (v) washing out unreacted fluorophore with said non-aqueous solvent.

17. The method of claim 16, said method further comprising eluting said derivatized oligonucleotides.

18. The method of claim 1, wherein said drying comprises passing air through said solid support.

* * * * *